US005714629A

United States Patent [19]
Schneider et al.

[11] Patent Number: 5,714,629
[45] Date of Patent: Feb. 3, 1998

[54] PROCESS FOR THE PREPARATION OF THIOGLYCOLIC ACID ALKYL ESTERS

[75] Inventors: Alexandra Schneider, Aschaffenburg; Gerhard Cimbollek, Seeheim; Bernd Muller, Zwingenberg; Ulrich Heywang, Darmstadt, all of Germany

[73] Assignee: Merck Patent Gesellschaft Mit Beschrankter Haftung, Darmstadt, Germany

[21] Appl. No.: 574,332

[22] Filed: Dec. 18, 1995

[30] Foreign Application Priority Data

Dec. 19, 1994 [DE] Germany .................. 44 45 202.0

[51] Int. Cl.⁶ .................................................. C07C 319/12
[52] U.S. Cl. ............................................................ 560/147
[58] Field of Search ................................................ 560/147

[56] References Cited

U.S. PATENT DOCUMENTS 4,380,650  4/1983  Coleman et al. .................... 549/326
5,095,138  3/1992  Labat et al. ........................ 550/147
5,124,490  6/1992  Cipullo ............................... 568/758

FOREIGN PATENT DOCUMENTS 53-65391  5/1978  Japan .

*Primary Examiner*—Samuel Barts
*Attorney, Agent, or Firm*—Millen, White, Zelano, & Branigan, P.C.

[57] ABSTRACT

The invention relates to an improved process for the preparation of thioglycolic acid alkyl esters by heating a reaction mixture which essentially comprises thioglycolic acid, an alcohol and an acid catalyst, the water formed being removed by distillation using a water separator, in which the resulting product mixture is passed over a basic ion exchanger, if appropriate after removal of the acid catalyst.

20 Claims, No Drawings

PROCESS FOR THE PREPARATION OF THIOGLYCOLIC ACID ALKYL ESTERS

The invention relates to an improved working up process in the preparation of thioglycolic acid alkyl esters by heating a reaction mixture which essentially comprises thioglycolic acid, an alcohol and an acid catalyst, the water formed being distilled off azeotropically using a water separator.

BACKGROUND OF THE INVENTION

Thioglycolic acid esters are used in the preparation of plastics, and in particular they counteract embrittlement of plastics under incident light.

Japanese laid-open specification JP 54 157504 proposes neutralization, with an aqueous alkaline solution, of the product mixture obtained in the esterification of carboxylic acids with an alcohol in the presence of an acid catalyst, and absorption of the remaining free acid on a strongly basic ion exchanger. However, waste waters polluted by the particular free acid are obtained in this procedure.

SUMMARY OF THE INVENTION

An object of the present invention was thus to provide a simplified process which allows thioglycolic acid alkyl esters to be made available in higher space/time yields.

A further object of the invention was to provide a process in which no waste waters polluted with thioglycolic acid can enter the environment.

Upon further study of the specification and appended claims, further objects and advantages of this invention will become apparent to those skilled in the art.

These objects have been achieved according to the invention by passing the product mixture obtained in the azeotropic esterification of thioglycolic acid over a basic ion exchanger, in particular a weakly basic ion exchanger, to remove traces of acid.

The invention therefor relates to a process for the preparation of thioglycolic acid alkyl esters by heating a reaction mixture which essentially comprises thioglycolic acid, an alcohol and an acid catalyst, the water formed being distilled off azeotropically using a water separator, characterized in that the resulting product mixture is passed over a basic ion exchanger, optionally after mechanical removal of the acid catalyst.

The term "alcohol" encompasses saturated, unsaturated, cyclic and acyclic alcohols of 1 to 12 carbon atoms. Preferably, the alcohol is a straight-chain or branched aliphatic alcohol having 2 to 12, preferably 5 to 10, C atoms, in particular branched $C_{6-10}$ alcohols, such as, for example, 2-ethylhexanol.

The term "basic ion exchanger" encompasses, for example, commercially obtainable anion exchangers. Preference is given to those which contain free amino groups of the formula —$N(R)_2$, wherein R is $C_{1-6}$-alkyl, on the polymer skeleton, in particular weakly basic, macroporous or gelatinous ion exchangers preferably having a particle size of from about 0.1 to 1.0 mm and a bulk density of from about 500 to 800 g/l, in particular 600 to 700 g/l, such as, for example, Amberlyst A-21.

The term "acid catalyst" generally represents acids which are not esterified under the conditions described, preferably mineral acids, such as, for example, hydrochloric acid or sulfuric acid, sulfonic acids, such as, for example, p-toluenesulfonic acid, or acid ion exchangers. Those acid catalysts which can escape during the process or, after the actual preparation process, can easily be removed from the product mixture by mechanical methods and thus do not lead to pollution of the basic ion exchanger are preferably employed.

Preferred embodiments of the process according to the invention are:

Processes in which the resulting product mixture after treatment with the basic ion exchanger is purified by distillation.

Processes in which 2-ethylhexanol is used as the alcohol.

Processes in which the reaction of the thioglycolic acid and alcohol is carried out at a temperature of about 60° to 150° C.

Processes in which the reaction is carried out under reduced pressure, preferably under pressures of from about 300 to 10 mbar.

Processes in which 1.0 to 1.5 mol, in particular 1.02 to 1.10 mol, of alcohol are employed per 1.0 mol of thioglycolic acid in the reaction.

Processes in which 0.01 to 0.1 parts by weight of acid catalyst is employed per one part by weight of thioglycolic acid in the reaction.

Processes in which an acid ion exchanger is employed as the acid catalyst, in particular Amberlyst A-15.

The term "acid ion exchanger" encompasses, for example, commercially obtainable polymeric cation exchangers, for example, styrenesulfonic acid polymers, such as Lewatit S 100, Zeo-Karb 225, Dowex 50, Amberlite IR 120 or Amberlyst A-15, polysulfonic acid condensates, such as Lewatit PN or Zeo-Karb 215 or 315, m-phenolcarboxylic acid resins, such as Lewatit CNO or Duolite CS 100, or polyacrylates, such as Permutit C, Zeo-Karb 226 or Amberlite IRC 50.

Particularly preferred acid ion exchangers are macroporous ion exchangers, in particular Amberlyst A-15 from Rohm & Haas or K 2631 from Bayer.

The procedure for the process according to the invention is simple per se. A mixture comprising thioglycolic acid, the alcohol and the acid catalyst is initially introduced into a first reactor. Optionally, the alcohol can also be added after a reduced pressure has been applied. The reaction mixture is heated at the boiling point, using a water separator, until no further water passes over. The product mixture is separated from the acid catalyst by filtration, if desired, and is passed or pumped continuously, without prior cooling, over a second reactor, particularly a fixed bed reactor, charged with the basic ion exchanger.

The reaction mixture is passed over the second reactor, i.e., the fixed bed reactor, until the starting material breaks through, i.e., until thioglycolic acid is detected in the product mixture (for example by titration with tetrabutylammonium hydroxide solution for determination of the free acid or by a thin layer, HPLC or gas chromatogram).

The crude product thus obtained from the second reactor charged with the basic exchanger is introduced into a distillation apparatus without prior cooling and is preferably distilled under reduced pressure, in particular under pressures from about 1 to 20 mbar, in particular from about 6 to 17 mbar.

After use of the basic ion exchanger several times, it may be washed and regenerated with a base.

On the basis of the process according to the invention, it is possible to prepare thioglycolic acid alkyl esters, an important product for the plastics-producing industry, in relatively high space/time yields, avoiding waste waters which pollute the environment. The process according to the invention furthermore has a favorable energy balance, since the product mixture does not have to be cooled to room temperature and heated again between the actual preparation process, the treatment with the basic ion exchanger and the distillation.

In the foregoing and in the following examples, all temperatures are set forth uncorrected in degrees Celsius; and, unless otherwise indicated, all parts and percentages are be weight.

The entire disclosure of all applications, patents and publications, cited above and below, and of corresponding German application No. P 44 45 202.0, filed Dec. 19, 1995, is hereby incorporated by reference.

EXAMPLES

The following example is intended to illustrate the invention without limiting it. The temperatures stated relate to degrees Celsius (° C.) and the pressures stated to millibars (1 mbar=0.75 mmHg).

Example

Preparation of Isooctyl Thioglycolate 5.6 g of Amberlyst A-15 are introduced into a stirred apparatus. 189.3 g (2.034 mol) of thioglycolic acid and 278.7 g (2.141 mol) of 2-ethylhexanol are added simultaneously. The mixture is heated at the boiling point under a pressure of 170 mbar, while stirring and using a water separator, until no further water passes over. After the water formed has been removed, the reaction mixture is cooled to 85° C. and the ion exchanger is separated off from the reaction mixture. The product mixture is then passed over a column with Amberlyst A-21. The basic ion exchanger used is employed further without regeneration. The residue is distilled under reduced pressure (8.5 mbar) at an overhead temperature of 105° C. 340.9 g (82% of theory) of the product are obtained with first runnings of 14.2 g and a residue of 35.5 g. No waste water polluted with thioglycolic acid is obtained in this procedure.

Comparison Example

A mixture of 2.5 g of Amberlyst A-15, 71.0 g (0.763 mol) of thioglycolic acid and 109.8 g (0.843 mol) of 2-ethylhexanol is heated as described in Example 1, using a water separator, until no further water passes over. The residue is neutralized with 15 ml of a 10% sodium bicarbonate solution at 25° C. and washed with 15 ml of a 3% sodium chloride solution. After the aqueous phase (31.9 g of wash water polluted with thioglycolic acid) has been removed, the residue is distilled under reduced pressure (8.5 mbar) at an overhead temperature of 105° C. 129.5 g (82%) of the product are obtained with first runnings of 16.1 g and a residue of 4.9 g.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A process for the preparation of a thioglycolic acid alkyl ester comprising: heating a reaction mixture comprising thioglycolic acid, an alcohol and an acid ion exchanger catalyst to produce a thioglycolic acid ester by reaction of thioglycolic acid and the alcohol, while distilling off the water formed during the reaction azeotropically.

2. The process of claim 1, wherein the alcohol is a straight-chain or branched aliphatic alcohol of 2 to 12 carbon atoms.

3. The process of claim 1, wherein the alcohol is a branched $C_6$-$C_{10}$ alcohol.

4. The process according to claim 1, wherein the alcohol is 2-ethylhexanol.

5. The process according to claim 1, wherein the reaction is carried out at a temperature off froth 60° to 150° C.

6. The process according to claim 1, wherein the reaction is carried out under reduced pressure.

7. The process according to claim 1, wherein 1.0 to 1.5 mol of alcohol are employed per 1.0 mol of thioglycolic acid.

8. The process according to claim 1, wherein 0.01 to 0.1 parts by weight of acid ion exchanger catalyst is employed per one part by weight of thioglycolic acid.

9. The process according to claim 1, wherein the acid catalyst is an acid ion exchanger.

10. The process of claim 1, wherein the acid ion exchanger is a styrenesulfonic acid polymer, polysulfonic acid condensate, m-phenolcarboxylic acid resin, or polyacrylate acid ion exchanger.

11. The process of claim 1, wherein the acid ion exchanger is a macroporous acid ion exchanger.

12. The process of claim 1, further comprising passing the resultant product mixture over a basic ion exchanger.

13. The process according to claim 12, wherein the basic ion exchanger is a weakly basic ion exchanger.

14. The process according to claim 12, wherein, after passing over the basic ion exchanger, the product mixture is purified by distillation.

15. The process of claim 12, wherein the basic ion exchanger is a basic ion exchanger containing free amino groups of the formula —$N(R)_2$, wherein R is $C_{1-6}$-alkyl, on a polymer skeleton.

16. The process of claim 12, wherein the basic ion exchanger has a particle size of 0.1 to 1.0 mm and a bulk density of 500 to 800 g/l.

17. The process of claim 16, further comprising mechanically removing the acid ion exchanger catalyst from the resultant product mixture before passing over the basic ion exchanger.

18. The process of claim 16, further comprising distilling the resultant product mixture after passing over the basic ion exchanger.

19. The process of claim 16, wherein the resultant product mixture is not cooled before passing over the basic ion exchanger.

20. The process of claim 18, wherein the resultant product mixture is not cooled either before passing over the basic ion exchanger or before distilling.

* * * * *